Figure 1:
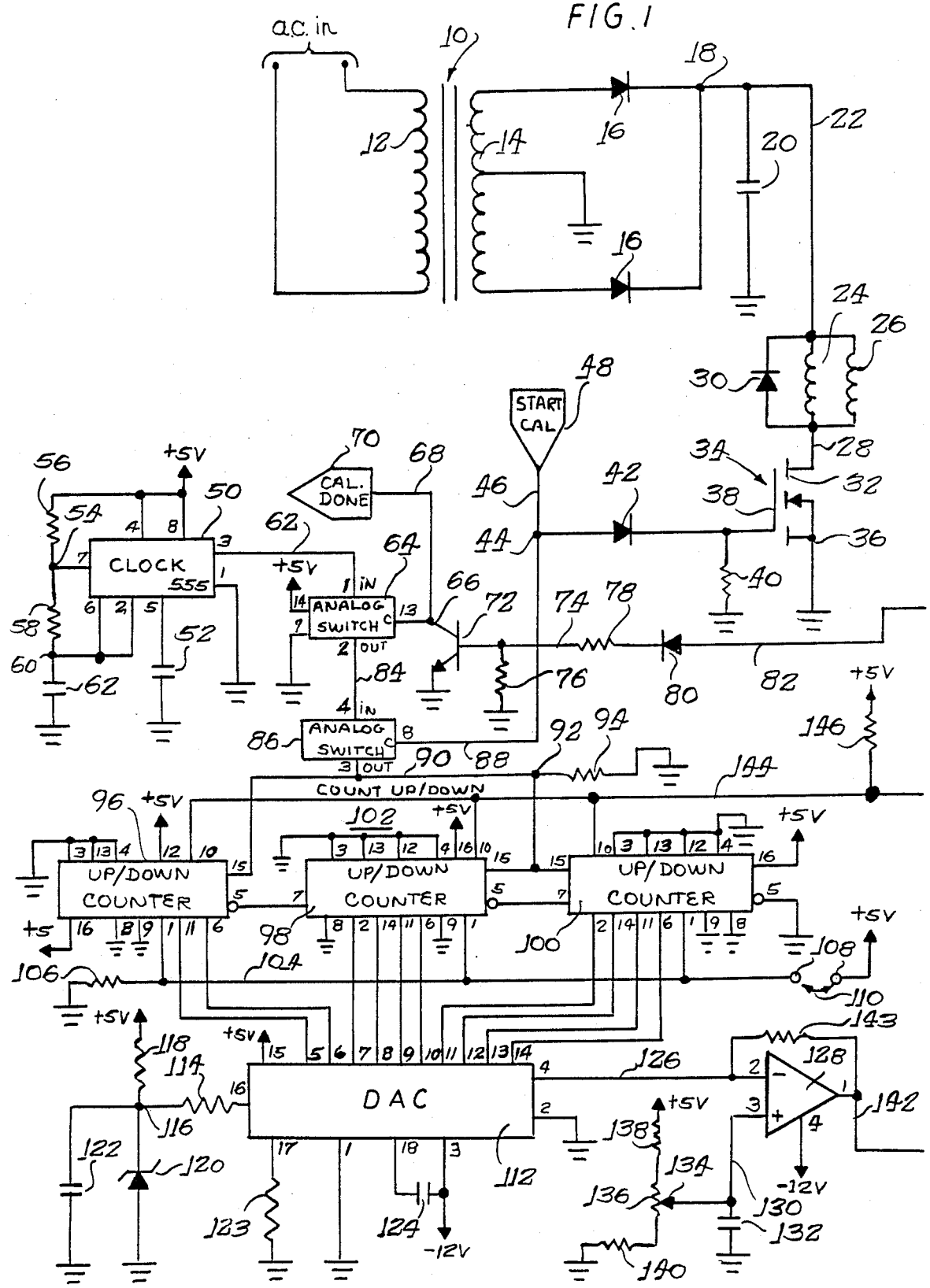

United States Patent [19]

Urman et al.

[11] Patent Number: 4,788,456

[45] Date of Patent: Nov. 29, 1988

[54] VARIABLE THRESHOLD FOR RATE VOLUME MONITOR

[75] Inventors: Robert Urman, Schaumberg; Alfred G. Brisson, Kildeer; Christopher Nowacki, Arlington Heights, all of Ill.

[73] Assignee: Trutek Research, Inc., Lake Zurich, Ill.

[21] Appl. No.: 77,746

[22] Filed: Jul. 27, 1987

[51] Int. Cl.$^4$ .................. H03K 5/153; H03K 5/24; H03K 17/30

[52] U.S. Cl. .................. 307/350; 307/290; 307/354; 307/359; 307/573

[58] Field of Search ............ 307/350, 352, 354, 358, 307/359, 573, 290

[56] References Cited

U.S. PATENT DOCUMENTS 4,358,738 11/1982 Kahn .................. 307/358
4,634,902 1/1987 Tanaka et al. .................. 307/573

OTHER PUBLICATIONS

P. R. Epley et al., "Schmitt Trigger Circuit" IBM Technical Disclosure Bulletin, vol. 16, No. 5, Oct. 1973, pp. 1600–1601.

Primary Examiner—John Zazworsky
Attorney, Agent, or Firm—Robert M. Wolters

[57] ABSTRACT

A variable threshold circuit is provided for use with a rate volume monitor. A series analog switch is controlled by a comparator which is biased by a voltage divider. During low rate exhalation by a patient the bias keeps the analog switch biased against conduction, and noise is suppressed. When exhalation is at a high rate a resistor is switched by a second analog switch into parallel with one of the resistors of the voltage divider to change the bias to the comparator, and thus to render the first analog switch conductive. At this time the high level of the exhalation signal masks any noise.

4 Claims, 2 Drawing Sheets

VARIABLE THRESHOLD FOR RATE VOLUME MONITOR

BACKGROUND OF THE INVENTION

In the testing of lung capacity and the ability of a person to inhale or to exhale it is known to use a Venturi device to produce an air pressure differential, and to use an air pressure-to-electric voltage transducer to provide an electric signal which is a function of inhaled or exhaled air velocity. A computer integrates the velocity over a period of time to provide an indication of the actual volume of air inhaled or exhaled. Sensitive transducers are expensive, and efforts therefore have been made to utilize relatively inexpensive transducers. Such transducers of this nature are relatively insensitive, and produce a rather low level electric output.

This low level electric voltage has required high amplification, and this has caused electrical noise to be a problem.

There are times when a patient is unable to breathe for himself, and he is placed on a breathing apparatus providing forced inhalation. In such instance the exhalation is monitored, since this is done voluntarily by the patient, and is necessarily of the same volume as inhalation.

Exhalation is a non-linear function. Initial exhalation is at a relatively high rate. Exhalation then tapers off considerably, eventually reaching a very low level. There are generally time gaps from the end of inhalation to the start of exhalation, and from the end of exhalation to the start of inhalation. The most useful information is produced at the start of exhalation As exhalation tapers off the information becomes less valuable. There obviously is no useful respiratory information produced during the gaps in time at either end of the exhalation.

Noise signals are most obtrusive during the low level and no level periods of exhalation, since they may be on the same order of magnitude, or of greater magnitude than the signal from the transducer. On the other hand, noise signals are totally masked by the transducer signal during the initial period of rapid exhalation.

OBJECTS AND SUMMARY OF THE PRESENT INVENTION

It is an object of the present invention to provide a variable threshold for a rate volume monitor, so that there will be a low threshold when there is a high signal level masking noise, and a high threshold when there is a low signal level.

In achieving the foregoing object we provide a variable threshold circuit that has an analog switch in series with the signal carrying circuit. This analog switch is controlled by the output of a comparison circuit which has a reference voltage provided by a series resistor type of voltage divider, and in which the signal is compared with this reference voltage. With a low signal, the analog switch is biassed for non-conduction, and noise signals have no effect at all. For higher signal levels the output of the comparison circuit changes and renders a second analog switch conductive to place an additional resistor in parallel with one of the voltage divider resistors, thus changing the reference voltage and rendering the first analog switch conductive.

THE DRAWINGS

Figure 2:
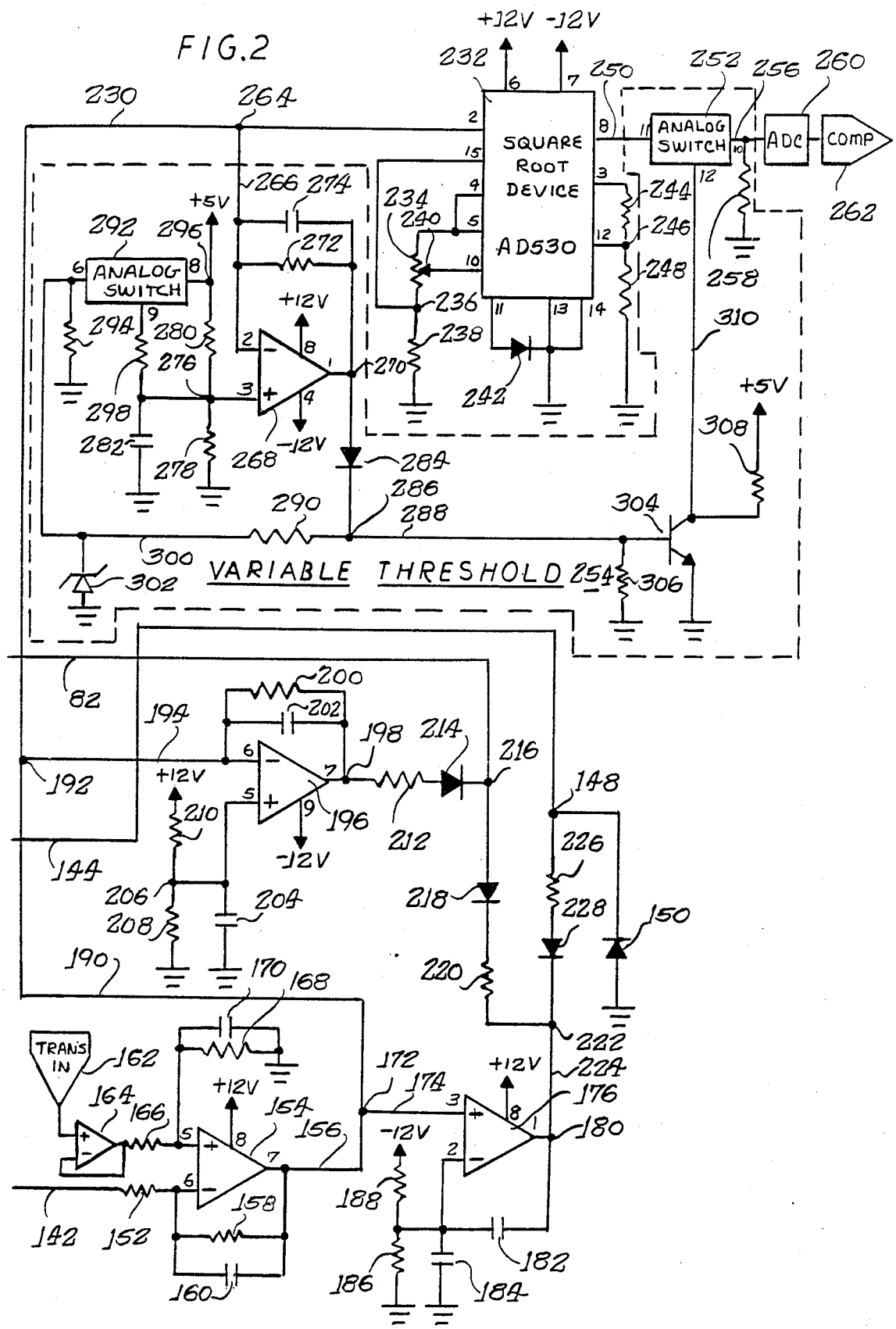

The present invention will best be understood from the following specification when read in connection with the accompanying drawings wherein:

FIG. 1 comprises an electronic wiring diagram consisting approximately one-half of the present disclosure; and FIG. 2 is another electronic wiring diagram representing the balance of the circuit.

FIGS. 1 and 2 are both to be retained in vertical position and FIG. 1 positioned immediately to the left of FIG. 2 for consideration of the complete circuit.

DETAILED DISCLOSURE OF THE ILLUSTRATED EMBODIMENT

Attention now should be directed to the upper portion of FIG. 1, wherein there is shown a transformer 10. The input winding 12 of the transformer is connected by a suitable wire or the like to an alternating current source of 120 volts, indicated as "a.c. in". The output winding coil 14 of the transformer has a center tap which is grounded. The opposite ends of the secondary winding are respectively connected to the anodes of solid state rectifiers 16, the cathodes of which are connected in common at 18 to a smoothing capacitor 20, and on to an output line 22. The output line 22 is connected in parallel to one end of each of a pair of relay coils 24 and 26. The opposite ends of these relay coils are connected in common to a conductor 28. A diode 30 parallels the two coils 24 and 26 with the cathode thereof connected to the line 22 and the anode connected to the conductor 28.

The output conductor 28 is connected to the drain 32 of a MOSFET transistor 34 having the source 36 connected to ground. The gate 38 of this transistor is grounded through a resistor 40, and also is connected to the cathode of a diode 42. The anode of the diode 42 is connected to a junctionpoint 44 on a line or conductor 46 which is provided with an input connection 48 from an accompanying computer which supplies a "start calibration" signal to the input connection 48.

A clock 50 is seen along the left margin of FIG. 1 and includes a general purpose electronic device 555 supplied by several manufacturers. The device is connected as shown with pin 1 being grounded, and pin 5 connected to ground through a capacitor 52. Pins 4 and 8 are connected to a +5 volt supply. Pin 7 is connected to the junction 54 between a resistor 56 and a resistor 58.

The opposite end of the resistor 56 is connected to the +5 volt supply, while the opposite end of the resistor 54 is connected to a junction 60. Pins 2 and 6 of the device are connected to the junction 60, and this junction is connected to a capacitor 62, the opposite side of which is grounded. The output pin, pin 3, of the type 555 device is connected by a line 62 to the input pin, pin 1, of an analog switch 64. Pin 14 of the analog switch is connected to the +5 volt supply, while pin 7 is grounded. Pin 13 is connected to a junction 66, which is in turn connected by a line 68 to an output connection 70 carrying a "calibration done" signal when calibration has been completed. The junction 66 also is connected to the collector of an n-p-n transistor 72, the emitter of which is connected to ground. The base is connected to a line 74 which is shunted to ground by a resistor 76, and is connected through a resistor 78 to the cathode of a diode 80. The anode of this diode is connected to a line 82, and this will be discussed further in connection with FIG. 2.

Pin 2, the output pin of the analog switch 64, is connected by a line 84 to input pin 4 of another analog switch 86. Control pin 8 is connected by a line 88 to the junction 44. Output pin 3 is connected to a line 90 which has a junction 92, and which is connected through a resistor 94 to ground. As will be recognized, the two analog switches 64 and 86 can be a common package.

Three up/down counters 96, 98 and 100 are connected as a ten bit up/down counter. Each of the four bit counters has pin 16 thereof connected to the +5 volt supply source. Pin 12 of counter 96 also is connected to the +5 volt supply source. However, Pin 12 of counters 98 and 100 is grounded, while pins 3, 4, 8, 9 and 13 of all three four bit counters are grounded. Pin 15 of each of the three four bit counters is connected to the line 90. Pin 1 of each of the four bit counters is connected to a line 104 which is connected at the left end through a resistor 106 to ground. At the right end the line has a pair of spaced contacts 108 through which it can be connected to the +5 volt source by a jumper 110 during factory calibration. Pin 5 of counter 96 is connected to pin 7 of counter 98, and pin 5 of counter 98 is connected to pin 7 of counter 100. Pin 5 of counter 100 is connected to ground.

The remaining pins of the three counters are connected as will be set forth immediately hereinafter to a digital-to-analog converter 112. Pin 15 of the digital-to-analog convertor is connected to the +5 volt supply source, while pins 1 and 2 are grounded. Pin 16 of the convertor is connected through a resistor 114 to a junction 116 between a resistor 118 and the cathode of a zener diode 120, the anode of which is grounded. A capacitor 122 shunts the junction 116 to ground. Pin 3 is connected to a −12 volt supply source, while Pin 18 is connected through a capacitor 124 to the −12 volt supply source. Pin 17 is grounded through a resistor 123.

Pins 11 and 6 of four bit counter 96 are respectively connected to pins 5 and 6 of the digital-to-analog convertor 112. Pins 2, 14, 11 and 6 of counter 98 are respectively connected to pins 7, 8, 9 and 10 of the convertor 112. Pins 2, 14, 11 and 6 of counter 100 are respectively connected to pins 11, 12, 13 and 14 of convertor 112.

Output pin 4 of the convertor 116 is connected by a line 126 to the inverting input of an operational amplifier (op amp) 128. The non-inverting input of the op amp 128 is connected to a line 130 which is connected to the upper end of a capacitor 132, the lower end being grounded. The line 130 also is connected to the sliding tap 134 on a potentiometer resistor 136. The top end of the potentiometer resistor 136 is connected through a resistor 138 to the +5 volt supply, while the lower end of the potentiometer resistor 136 is connected through a resistor 140 to ground. As will be apparent, the bias to the non-inverting input of the op amp 128 can be controlled by moving the tap 134 on the resistor 136. The output returns to the inverting input through a resistor 143.

The op amp 128 is provided with a −12 volts bias potential connected to pin 4, while the output is connected to a line 142. The output of the digital-to-analog convertor 112 on line 126 is on the order of 0 to 25 microamps during calibration at approximately 125 millivolts. The current is converted to voltage by the op amp 128, and the output of this op amp is in the range of 0 to 2 volts.

Pin 10 of each of the counters 96, 98 and 100 is connected to a line 144 which leads through a resistor 146 to the +5 volt supply source. This line continues on FIG. 2 to a junction 148 which is connected to the cathode of a diode 150, the anode being grounded.

Turning now to sheet 2 of the drawings, the line 142 continues through a resistor 152 to the inverting input of an operational amplifier 154 having a +12 volt bias as indicated. The output of the operational amplifier 154 is taken on a line 156, and is returned to the inverting input through the combination of a resistor 158 and a capacitor 160 in parallel with the resistor.

The electrical input from the air pressure to voltage transducer is indicated at 162, and it is connected to the non-inverting input of an operational amplifier 164. The output of the operational amplifier 164 is connected back to the inverting input thereof, and is connected through a resistor 166 to the non-inverting input of the operational amplifier 154. The non-inverting input is shunted to ground by a resistor 168 and a capacitor 170 in parallel therewith.

The line 156 is provided with a junction point 172, and a line 174 extends from this junction point to the non-inverting input of an operational amplifier 176. This op amp is provided with a +12 volts bias as indicated. The output is connected to a junction 180, and the junction is returned to the inverting input through a capacitor 182. The inverting input is shunted to ground through a capacitor of 184 and a resistor 186, the resistor forming a voltage divider with a resistor 188 connected to a −12 volts supply for biasing the inverting input.

A line 190 leads from the junction 172 to a junction 192, the latter being connected by a line 194 to the inverting input of an operational amplifier 196. The output at 198 of this op amp is returned through the parallel combination of a resistor 200 and a capacitor 202 to the inverting input. The op amp 196 is biased with a −12 volts as indicated. The non-inverting input is shunted to ground by a capacitor 204. The non-inverting input also is connected to the junction point 206 between a grounded resistor 208 and a resistor 210 leading to a +12 volt supply.

The output junction 198 is connected through a resistor 212 to the anode of a diode 214, the cathode thereof being connected to a junction 216. This junction is connected to the anode of a diode 218, the cathode of which is connected through a resistor 220 to a junction 222 connected by a line 224 to the junction 180. The previously mentioned junction 148 is connected through a resistor 226 to the anode of a diode 228, having the cathode thereof connected to the junction 222. It will be recalled that the junction 148 is connected to the line 144 leading back to the count up/down inputs of the counters 96, 98 and 100.

The line 190 continues beyond the junction 192 as a line 230 leading to the input pin of a square root device 232. The input is on pin 2, and the device is a type AD530. Pin 6 of the device is connected to a positive 12 volt supply, while pin 7 is connected to a −12 volt supply. Pin 4 is connected to pin 5, and both are connected to a potentiometer resistor 234, the opposite end of which is connected to a junction 236 which is in turn connected through a resistor 238 to ground. Pin 15 is connected to the junction 236. The variable tap 240 on the potentiometer is connected to pin 10.

Pin 11 is connected to the anode of a diode 242, having the cathode thereof grounded. Pins 13 and 14 are connected direct to ground. Pin 3 is connected to the top of a resistor 244 connected at a junction 246 to a resistor 248 leading to ground. Pin 12 is connected to the junction 246. The output is taken from pin 8 and is connected by a wire or other conductor 250 to the input of an analog switch 252. The analog switch comprises a part of a variable threshold circuit 254 to be described immediately hereinafter. The square root device is provided because the electrical output of the transducer to the input connection at 162 operates on a square law, and this produces a greatly expanded scale. The square root device reduces this to a linear scale, whereby the input to the analog switch 252 is a linear input. The output of the analog switch at 256 therefore is a linear output. The output is shunted to ground by a resistor 258, and is also connected to an analog-to-digital convertor 260 which in turn is connected to the computer at 262.

The remainder of the circuit, as noted, comprises a variable threshold circuit. The variable threshold circuit provides a relatively low threshold when there is a low signal, thereby substantially eliminating noise, but has a higher threshold when there is a higher level signal.

The line 230 is connected at a junction 264 to a line 266 leading to the inverting input of an operational amplifier 268. This operational amplifier is provided both with a +12 volt bias and a −12 volt bias, as indicated. The output is connected to a junction 270 which is returned to the inverting input by the parallel combination of a resistor 272 and a capacitor 274.

The non-inverting input of the op amp 268 is connected to a junction 276 on a voltage divider, comprising a grounded resistor 278, and a resistor 280 leading to a +5 volt supply. The grounded resistor 278 is paralleled by a capacitor 282.

The output 270 from the op amp 268 is connected to the anode of a diode 284 leading to a junction 286 on a line 288. The line is connected to a resistor 290 which leads to the input of an analog switch 292. This input is shunted to ground by a resistor 294. The output of the analog switch is connected to a junction 296 at the top of the resistor 280. The control element of the analog switch 292 is connected through a resistor 298 to the junction 276 leading to the non-inverting input of the op amp 268. The line 300 from the resistor 290 to the input of the analog switch 292 is limited to 5 volts or less through connection to the cathode of a zener diode 302, the anode of which is grounded.

The line 288 leads to the base of an n-p-n transistor 304, the emitter of which is grounded. The input to the base is shunted by a grounded resistor 306. The collector is connected through a resistor 308 to a +5 volt supply, while the collector also is connected through a line 310 to the control element of the analog switch 252.

Calibration Operation

The object of the calibration is to avoid drift of the voltage provided by the transducer at 162, or more particularly to avoid the effects of drift at this input position. This is done by periodically adjusting the voltage at the inverting input to the operational amplifier 154 to equal the voltage at the non-inverting input thereof. When there is no airflow through the transducer, the output on line 156 of the operational amplifier 154 will be zero if the two inputs are equal.

On a regular timed basis the computer provides a signal to the start calibration input at 48. This may, for example, be at every 10 minutes, and the signal goes high. This high signal passes through the diode 42 and the transistor 34 to energize the coils 24 and 26. This opens the connection between the Venturi and the transducer, and vents transducer to atmosphere. This produces zero pressure across the transducer, the same as zero airflow, and the potential at the transducer in position 162 is whatever the transducer settles to at no flow.

With the start calibration input 48 high, the analog switch 86 is turned on. Whatever appears on the input pin 4 goes through to the output pin 3. There is a clocking signal applied from the clock 50 to the input pin 1 at a predetermined frequency on the order of 1 KHz and it is a square wave. The clock signal does not initially pass through the analog switch 64 as the input at point 13 is such as to maintain the switch open.

The input to the inverting input of the op amp 154 is not yet known at the start of calibration. The output of this op amp on line 156 is either zero, or not zero. The zero need not be absolute, and can be on the order of ±1.5 mv. The not zero condition can be either plus or minus. If the output is not zero or within the zero band, then the output of op amp 176 will change accordingly. This will produce a bias on the base of transistor 72 which will cause this transistor to be turned off. This will cause control pin 13 of analog switch 64 to go high. This biases analog switch 64 for conduction, whereby the clock input is fed through to the binary up/down counters 96, 98 and 100. The combined counter 102 counts up or down as determined by the potential on the up/down line 144. This is controlled by the output of op amp 176. If pin 5, the non-inverting input of op amp 176, is higher than pin 6, the inverting input, then it is necessary to raise pin 6 potential to equal that of pin 5, so the counter 102 counts up. If pin 5 is lower than pin 6, then the counter is to count down.

The output of the counter 102 is converted by the digital to analog convertor 112 to a current, and this is converted to a voltage by the op amp 128. Thus, there is an analog voltage out of pin 1 of op amp 128. It will be seen that the up/down counter 102, the digital to analog convertor 112, and the op amp 128 constitute essentially a digital potentiometer. Clocking continues until pin 7 of op amp 154 reaches zero. The biasing produced by the combination of op amps 154 and 196 then is such as to turn on transistor 72, thereby opening analog switch 64. This also places an output signal on the calibration done connection 70 which tells the computer that the correction has been completed.

Since it is not known in advance which way drifts of the input signal at 162 from the transducer will be, plus or minus, the output of the digital-to-analog computer 112 initially should be in the middle of its range. This is effected during factory calibration by shorting the contacts 108 by means of the shorting device 110, thereby applying +5 volts to pin 1 of each of the counters 96, 98 and 100, this pin being a preset enable pin. The counter is capable of counting from 2 to the 0 power up to 2 to the 9th power, i.e. from 10 zeros to 10 ones. Thus, to achieve a midpoint, a count should show one followed by nine zeros. Thus, the current output on pin 4 of the digital to analog computer connects to digital analog convertor 112 will be 12.5 micro amperes. Potentiometer 134, 136 is used for calibration and is adjusted until output pin 7 of op amp 154 is at zero.

Operation of the Variable Threshold Circuit

When calibration is completed and monitoring of the patient's respiration is resumed, there will be a variable input at 162 which will be amplified by the op amp 154 and appear on the line 190, continuing on the line 230 through the square root device to the analog switch 252. Whether this switch conducts or not is determined by the variable threshold circuit 254. This circuit adjusts for glitches in the wave form by effectively getting rid of them.

Prior to exhalation by the patient the voltage on lines 190 and 230 will be zero, and pin 3 of op amp 268 will be higher than pin 2. The op amp therefore has an output of +12 volts. This potential is passed through the diode 284 to junction 286, and on and through resistor 290, being limited to 5 volts by the zener diode 302. This causes the 5 volts potential to be applied to pin 6 of the analog switch 292, thus turning on the analog switch, and placing resistor 298 in parallel with resistor 280. The +12 volts output potential of the op amp 268 also is connected to the base of the transistor 304, turning this transistor on, and placing pin 12 of the analog switch 252 at zero potential, thereby opening this analog switch so that there is no output supplied to the computer at point 262.

When the patient exhales pin 2 of op amp 268 almost immediately becomes higher than pin 3. The output potential of the op amp 268 on pin 1 thereupon becomes negative. The analog switch 292 therefore is turned off, therefore removing resistor 298 from its parallel relationship with resistor 280. Transistor 304 also is turned off, and this turns the analog switch 252 on.

With the removal of the resistor 298 from the circuit by switching off of the analog switch 292 voltage on pin 3 of op amp 268 drops. This makes a greater differential in the voltage between pin 3 and pin 2. The voltage on pin 2 lowers as exhalation tapers off, and eventually the potential on pin 2 becomes less than that on pin 3. At that point the output of op amp 268 switches to +12 volts, again turning on transistor 304 and turning off the analog switch 252, and hence terminating input to the computer at 262. At the same time the analog switch 292 is again turned on, again placing resistor 298 in parallel with resistor 280. This raises the voltage on pin 3 back to the onset threshold and operation starts over.

Thus, there are two thresholds produced by the circuit. Specifically, when the resistor 298 is connected in parallel with the resistor 280 by the analog switch 292 there is a rather high threshold. Noise signals therefore cannot get through the switched off analog switch 252. However, once the analog switch 292 is turned off and resistor 298 is removed from parallel condition with the resistor 280 the threshold drops to a much lower level. Noise signals at this time are unimportant since there is a very strong signal which easily overrides any noise.

Those skilled in the art will readily be able to assign proper values to the resistors and capacitors referred to herein. However, recommended exemplary values are as follows:

| Resistors - in ohms | Capacitors - in micro farads |
|---|---|
| 56–4.7K | 20–220 |
| 58–4.7K | 52–.01 |
| 76–68K | 62–.1 |
| 78–10K | 122–.1 |
| 94–100K | 124–.01 |
| 106–68K | 132–.1 |
| 114–200K | 160–.22 |
| 118–2.2K | 170–.1 |
| 123–200K | 182–.05 |
| 136–5K | 184–1.0 |
| 138–51K | 204–1.0 |
| 140–3.9K | 202–.05 |
| 143–10K | 274–.05 |

-continued

| Resistors - in ohms | Capacitors - in micro farads |
|---|---|
| 146–27K | 282–.01 |
| 152–1K | |
| 158–4.7K | |
| 166–1K | |
| 168–4.7K | |
| 186–75 | |
| 188–560K | |
| 200–100K | |
| 208–75 | |
| 210–560K | |
| 212–2.7K | |
| 220–2.7K | |
| 226–2.7K | |
| 234–5K | |
| 238–5.1K | |
| 244–100 | |
| 248–100 | |
| 258–100K | |
| 272–100K | |
| 278–100K | |
| 280–47K | |
| 290–6.8K | |
| 294–68K | |
| 298–47K | |

The specific example of the invention as herein shown and described is for illustrative purposes only. Various changes will no doubt occur to those skilled in the art, and will be understood as forming a part of the present invention insofar as they fall within the spirit and scope of the appended claims.

The invention is claimed as follows:

1. A variable threshold circuit for use with a signal transmission circuit carrying a varying D.C. signal having a high amplitude portion carrying information of high significance and a low amplitude portion carrying information of lesser significance, comprising switch means connected to said signal carrying circuit in series therewith, reference voltage means providing a predetermined reference voltage, voltage comparing means having two inputs and an output, said reference voltage means being connected to one of said inputs, means connecting said transmission circuit to the other of said inputs to compare said signal and said reference predetermined voltage, means connecting said comparing means output to said switch means to bias said switch means for non-conduction of said signal during the low amplitude portion of said signal, said comparing means output being connected to said reference voltage means and during the high amplitude voltage portion of said signal being effective to change said reference voltage and thereby to change the voltage on the output of said comparing means to bias said switch means for conduction of said signal during the high amplitude portion of said signal, said reference voltage means comprising a first resistor connected to a predetermined supply voltage and to a junction and a second resistor connected to said junction and to a voltage reference, said junction being connected to said one of said inputs, a third resistor, and means connecting said comparing means output to said first resistor and to said third resistor to connect said third resistor in parallel with said first resistor so as to raise the voltage on said junction during the high amplitude portion of said signal, said third resistor being not so connected during the low amplitude portion of said signal.

2. A variable threshold circuit as set forth in claim 1 wherein said switch means comprises an analog switch.

3. A variable threshold circuit as set forth in claim 1 wherein said connecting means comprises switch means.

4. A variable threshold circuit as set forth in claim 3 wherein the connecting means switch means comprises an analog switch.

* * * * *